United States Patent [19]

Wong

[11] Patent Number: 4,766,180

[45] Date of Patent: Aug. 23, 1988

[54] CROSSLINKED ELASTOMERS CONTAINING BENZOCYCLOBUTENE DERIVATIVES AS CROSSLINKING AGENTS

[75] Inventor: Pui K. Wong, Katy, Tex.

[73] Assignee: Shell Oil Company, Houston, Tex.

[21] Appl. No.: 946,131

[22] Filed: Dec. 23, 1986

Related U.S. Application Data

[63] Continuation of Ser. No. 812,422, Dec. 23, 1985, abandoned.

[51] Int. Cl.[4] ...................... C08C 19/28; C08F 255/06
[52] U.S. Cl. .................................... 525/289; 525/313; 525/316; 525/319; 525/326.1; 525/331.7; 525/332.5
[58] Field of Search ................... 525/289, 326.1, 331.7, 525/332.5, 920, 925

[56] References Cited

U.S. PATENT DOCUMENTS

| | | | |
|---|---|---|---|
| 3,497,483 | 2/1970 | Ketley | 260/79.5 |
| 4,540,763 | 9/1985 | Kirchhoff | 526/281 |
| 4,638,078 | 1/1987 | Kirchhoff | 558/414 |
| 4,642,329 | 2/1987 | Kirchhoff | 526/284 |
| 4,661,193 | 8/1987 | Kirchhoff | 156/307.3 |

OTHER PUBLICATIONS

Elastomers, Synthetic, Kirk–Othmer Encyclopedia of Chemical Technology, vol. 7, pp. 677–716 (1965).
Boekelheide et al, Tetrahedron Lett. 1978, 4245–8.
Boekelheide, Topics in Current Chem. 1983, 113, 100–4.
Perkins et al., Angew. Chem. Int. Ed. Engl. 1978, 17(8), 615–6.
Ewing et al., J. Chem. Soc., Chem. Commun. 1979, 207.
Gray et al., J. Am Chem. Soc. 1978, 100, 2892–3.
Harruff et al., J. Am Chem. Soc. 1978, 100, 2893–4.
Aalbersberg, Tetrahedron Lett. 1979, 22, 1939–2.
Hubert et al., J. Che. Soc. 1965, 3160.
DeCamp et al., Tetrahedron Lett. 1974, 40, 3575–8.
Jenson et al., J. Am. Chem. Soc. 1958, 80, 6149.
Jensen et al., Tetrahedron Lett. 1962, 1, 15–18.
Klundt, Chem. Rev. 1970, 70(4), 471.
Tan et al., 1985 ACS Meeting, Chicago, Sep. 8–13, 1985, ACS Polymer Preprint 1985, 26(2), 176, 178.
Arnold et al., 31st Int. SAMPE Symposium, Apr. 7–10, 1986, Preprint 1986, 968–976.
Tan et al., 1986 ACS Meeting, Apr. 13–18, 1986, ACS Polymer Preprint 1986, 27(1), 453–4.
Tan et al., 1987 ACS Meeting, Denver, Apr. 5–10, 1987, ACS Polymer Preprint, 1987, 28(1), 650–5.
Denny et al., 1987 ACS Meeting, Denver, Apr. 5–10, 1987, ACS Polymer Preprint, 1987, 28(1), 656–9.

*Primary Examiner*—Wilbert J. Briggs, Sr.

[57] ABSTRACT

Polymeric compositions which may be readily crosslinked at temperatures above about 200° C. comprise an elastomeric polymer possessing olefinic unsaturation and an effective amount of a benzocyclobutene derivative of the general formula

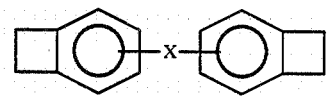

where "X" is selected from the group consisting of

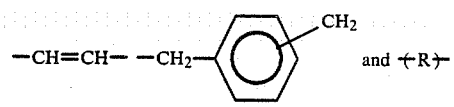

where "R" is an alkylene group of 1 to 10 carbon atoms. Cured compositions are also claimed.

19 Claims, No Drawings

CROSSLINKED ELASTOMERS CONTAINING BENZOCYCLOBUTENE DERIVATIVES AS CROSSLINKING AGENTS

This is a continuation of application Ser. No. 812,422, filed Dec. 23, 1985, now abandoned.

FIELD OF THE INVENTION

The present invention relates broadly to crosslinked elastomers and processes for preparing the same. More particularly, this invention relates to polymeric compositions comprising an elastomer and certain benzocyclobutene derivatives.

BACKGROUND OF THE INVENTION

As described in the article "Elastomers, Synthetic", Kirk-Othmer Encyclopedia of Chemical Technology, Vol. 7, pages 677-716 (Interscience Publisher 1965), "Synthetic elastomers are a group of synthetic high polymeric materials with properties that, in the past, might have been described as rubbery." The ASTM definition for rubber (1964 Book of ASTM Standards, ASTM D1566-62T) appears to also cover elastomers. This definition, which is based on physical characteristics and not on chemical structure, defines a rubber as "a material that is capable of recovery from large deformations quickly and forcibly and can be, or already is, modified to a state in which it is essentially insoluble (but can swell) in boiling solvents such as benzene, methyl ethyl ketone, and the ethanol-toluene azeotrope. A rubber in its modified state, free of diluents, retracts within one minute to less than 1.5 times its original length after being stretched at room temperature (20°-27° C.) to twice its length and held for one minute before release."

With a few exceptions, elastomers are not typically employed in their raw or dry state. For the great majority of uses, the elastomer must be modified, usually by the addition of crosslinking or curing agents, followed by a heat cure.

One common elastomer of general utility is ethylene-propylene-diene monomer terpolymer (EPDM). EPDM polymers are desirable elastomers since they are prepared from low-cost monomers and have good mechanical and elastic properties as well as outstanding resistance to ozone, heat and chemical attack.

EPDM polymers may be sulfur-cured but usually require ultra-accelerators in the recipe because of the low-polymer unsaturation. EPDM can be vulcanized with systems based on sulfur, peroxides, quinoids, or polyhalomethyl resins. Some of the best current systems contain sulfur (1.5 phr), zinc oxide (5 phr), stearic acid, a primary accelerator (thiuram mono-, di- or tetrafulfides or metal salts of a dithiocarbamic acid (1.5 phr)), and a thiazole (0.5 phr) as a secondary accelerator. High oil and black levels can be accepted. With recipes such as these, satisfactory cures for some applications may be obtained in the usual times and temperatures (e.g., 30 min. at 320° F.).

Peroxide curing of EPDM elastomers is the most common system. Peroxide curing involves coupling of allylic radicals derived from the cure site monomer and peroxide generated radicals to give vulcanizates containing allylic carbon-carbon bonds. This curing system is not desirable for certain applications. For example, when such EPDM elastomers are used as seals in high temperature applications (above about 300° C.), the peroxide-cured EPDM elastomers may fail.

What is needed is a new method to cure such elastomers, that result in cured or vulcanized products (e.g. seals) that have improved thermal stability and higher cure temperatures.

SUMMARY OF THE INVENTION

The present invention relates broadly to a polymeric composition which may be readily crosslinked or cured at certain temperatures to produce polymeric products having an improved balance of properties. In particular, the present invention relates to a polymeric composition which may be readily crosslinked or cured at temperatures above about 200° C., said composition comprising an elastomeric polymer possessing olefinic unsaturation and an effective amount of a benzocyclobutene derivative of the general formula:

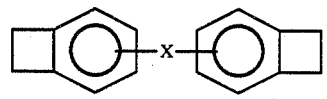

where "X" is selected from the group consisting of

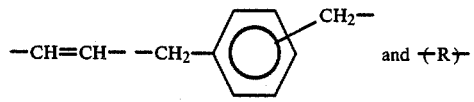

where R is an alkylene group of 1 to 8 carbon atoms.

As shown in the examples which follow, the current invention eliminates the use of sulfur and peroxide curing agents which introduce thermally weak and hydrolytically unstable linkages. In addition, the invention would lead to a reduction or elimination of weak allylic structures in the cured polymer and consequently may provide enhanced thermal stability. See H. J. Harwood, J TEVA, II, 289 (1983).

DETAILED DESCRIPTION OF THE INVENTION

There are two essential components to the present invention—an elastomer and a particular benzocyclobutene derivative.

Elastomer

One of the essential components of the present invention is an elastomer having olefinic unsaturation. Such elastomers include the following groups:
ethylene/$C_3$ to $C_8$ alpha-monoolefin/diene monomer terpolymers (EPDM)
butyl rubber
polyisobutylene
polybutadiene
polyisoprene
styrene-butadiene rubber
nitrile rubber
neoprene rubber
styrene-butadiene block copolymers.

Of the above elastomers, EPDM is the preferred elastomer.

EPDM terpolymer (being broader than ethylene, propylene, diene monomer terpolymers) useful for this invention comprise ethylene, a $C_3$ to $C_8$ straight or branched chain alpha-olefin and a diene. Representative non-limiting examples of non-conjugated dienes that may be used as the third monomer in the terpolymer include:

(a) Straight chain acyclic dienes such as: 1,4-hexadiene; 1,5-heptadiene, 1,6-octadiene.

(b) Branched chain acyclic dienes such as: 5-methyl-1,4-hexadiene; 3,7-dimethyl 1,6-octadiene; and 3,7-dimethyl 1,7-octadiene.

(c) Single ring alicyclic dienes such as: 1,4-cyclohexadiene; 1,5-cyclooctadiene; 1,5-cyclododecadiene, 4-vinylcyclohexene; 1-allyl,4-isopropylidene cyclohexane; 3-allyl-cyclopentene; 4-allyl cyclohexene and 1-isopropenyl 4-(4-butenyl)cyclohexane.

(d) Multi single ring alicyclic dienes such as: 4,4'-dicyclopentenyl and 4,4'-dicyclohexenyl dienes.

(e) Multi-ring alicyclic fused and bridged ring dienes such as: tetrahydroindene; methyl tetrahydroindene; dicyclopentadiene; bicyclo(2.2.1)hepta-2,5-diene; alkenyl, alkylidene, cycloalkenyl and cycloalkylidene norbornenes such as: 5-methylene-6-methyl-2-norbornene; 5-methylene-6,6-dimethyl-2-norbornene; 5-propenyl-2-norbornene; 5-(3-cyclopentenyl)-2-norbornene and 5-cyclohexyldene-2-norbornene.

In general, useful terpolymers contain non-conjugated dienes having 5 to 14 carbon atoms and exhibit weight average molecular weights of from 70,000 to 1,000,000 e.g., 70,000 to 150,000. Preferred dienes include ethylidene norbornene, dicyclopentadiene and 1,4 hexadiene. Structurally, the terpolymers suitable for the present invention may be illustrated for various non-conjugated diene monomers as random terpolymers in which the following moieties are linked in the polymer chain in a random sequence and in a varying number.

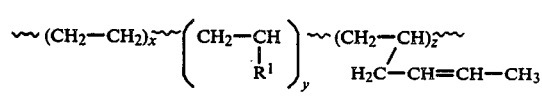

Ethylene units    Higher α-olefin units    1,4-hexadiene units (1)

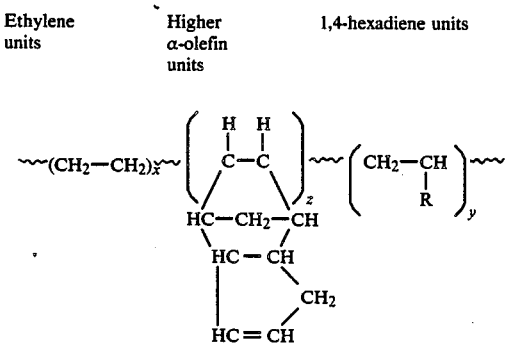

Ethylene units    Dicyclopentadiene units    Higher α-olefin units (2)

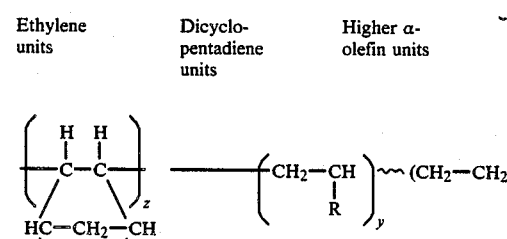

5-ethylene-2-norbornene    Higher α-olefin units    Ethylene units (3)

in which x, y and z are cardinal numbers. While these terpolymers are essentially amorphous in character by superficial inspection, they may contain up to about 25 percent by weight of crystalline segments as determined by X-ray of differential scanning calorimetry. Details of these methods for measurement of crystallinity are found in J. Polymer Science, A-2, 9, 127 (1971) by G. Ver Strate and Z. W. Wilchinsky. Terpolymers, useful in the present invention contain at least 30 mol percent, preferably not more than 85 mol percent of ethylene; between about 15 and about 70 mol percent of a higher alphaolefin or mixture thereof, preferably propylene; and between 1 and 20 mol percent, preferably 1 to 15 mol percent, of a non-conjugated diene or mixture thereof. Especially preferred are polymers of about 40 to 70 mol percent ethylene, 20 to 58 percent higher moloolefin and 2 to 10 mol percent diene. On a weight basis, usually the diene will be at least 2 or 3 wt. percent of the total terpolymer.

Other elastomers of this group are isobutylene polymers including solid polyisobutylene and butyl rubber. Butyl rubber is a high molecular weight copolymer of isobutylene with less than 20 percent, preferably less than 5 percent of one or more $C_4$-$C_{14}$ diolefins such as isoprene, divinyl benzene and pentadiene-1,4. See, generally U.S. Pat. No. 3,137,643. Another elastomer is high molecular weight synthetic polybutadiene such as that described in U.S. Pat. No. 3,317,918. Another synthetic elastomeric polymer is neoprene. These neoprene rubbers are typically produced from the polymerization of chloroprene(2-chloro-1,3-butadiene) and those copolymers produced by the polymerization of chloroprene and a constituent selected from the group consisting of styrene, isoprene, and acrylonitrile wherein the major component of the said produced copolymer is chloroprene. A chloroprene polymer can conventionally be produced by emulsifying the chloroprene in water by means of a sodium rosinate soap and polymerizing the chloroprene at 40° C., with the aid of potassium persulfate as a catalyst and in the presence of elemental sulfur as a modifier. Other similar polymers may be employed as well. See generally the Kirk-Othmer reference cited in the background of the invention and "Styrene-Butadiene Solution Copolymers", Kirk-Othmer Encyclopedia of Chemical Technology, Supplement Volume, pages 910–932 (Interscience Publishing 1971).

Benzocyclobutene Derivative

The second essential component in the present invention is a benzocyclobutene derivative of the general formula:

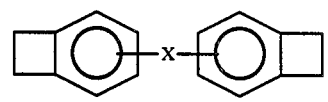

where "X" is selected from the group consisting of

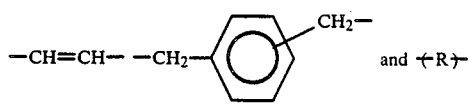

where R is an alkylene group of 1 to 10 carbon atoms.

In a preferred embodiment, the benzocyclobutene ("BCB") derivative is selected from the group consisting of 4,4'-ethylenedibenzocyclobutene, 4,4'-(p- xylylene)dibenzocyclobutene, 4,4'-(o-xylylene)dibenzocyclobutene, 4,4'-(m-xylylene)dibenzocyclobutene, 3,3'-(p-xylylene)dibenzocyclobutene, 3,3'-(o-xylylene)-dibenzocyclobutene, 3,3'-(m-xylylene)dibenzocyclobutene, 4,3'-(p-xylylene)dibenzocyclobutene, 4,3'-(o-xylylene)dibenzocyclobutene, 4,3'-(m-xylylene)dibenzocyclobutene, 4,4'-methylenedibenzocyclobutene, 3,3'-methylenedibenzocyclobutene and 4,3'-methylenedibenzocyclobutene. The xylylene and methylene derivatives are more preferred because they do not contain weaker benzylic bonds.

Process

The elastomer and the BCB are preferably mixed by combining the various ingredients in any suitable manner including solution blending, melt blending and dry blending.

An effective amount of BCB is employed. By the term "effective amount" is meant the resulting blends of BCB and rubbers can be cured by treating at temperatures >200° C. to give insoluble elastomers with acceptable mechanical properties. Preferably, the amount of BCB employed is between 1 and 30 percent by weight based on the amount of elastomer employed, more preferably between 5 and 20 percent by weight.

The polymer blends of the instant invention may be compounded further with other polymers, oils, fillers, reinforcements, antioxidants, stabilizers, fire retardants, antiblocking agents and other rubber and plastic compounding ingredients without departing from the scope of this invention.

The compositions of the present invention—comprising in broad terms an elastomer component and a benzocyclobutene derivative component—may be formed into a variety of applications including elastomeric seals, automotive components, belts, etc.

A key aspect of the present invention is that curing of the compositions occur when the compositions or parts are heated to a temperature above about 200° C. As shown in the following scheme, the presently claimed crosslinking technique is believed to proceed by the thermal ring opening of benzocyclobutenes to o-xylylenes which then add to the unsaturated elastomer via Diels-Alder reaction. Since the Diels-Alder cycloaddition would reduce or eliminate thermally weak allylic carbon-carbon bonds, the new curing chemistry will lead to elastomers with enhanced thermal stability and higher service temperature.

CURING SCHEME

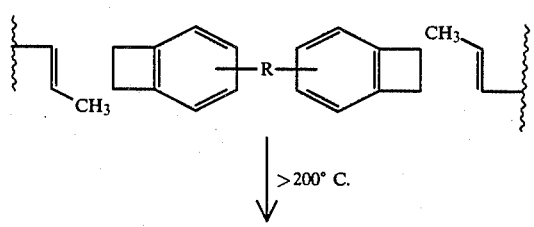

-continued
CURING SCHEME

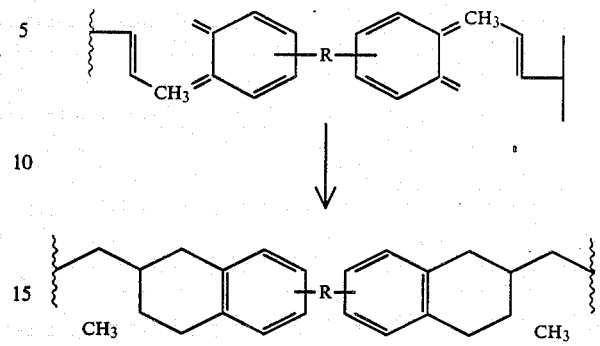

Crosslinking or curing or vulcanization (all terms meaning one and the same) is accomplished by heating the blended compositions to temperatures above about 200° C., preferably between about 200° C. and about 300°, more preferably between about 200° C. and about 250° C., for sufficient time to result in crosslinking. The time required depends in part upon the temperature employed, the amount of benzocyclobutene derivative employed, and the type of elastomeric component used. Typical curing times are 5 to 120 minutes at about 250° C. temperature.

To illustrate the instant invention, the following illustrative embodiments are given. It is to be understood, however, that the embodiments are given for purpose of illustration only and the invention is not to be regarded as limited to any of the specific materials or conditions used in the specific embodiments.

ILLUSTRATIVE EMBODIMENT I

A key aspect of the present invention deals with the ring-opening of the benzocyclobutene monomers to reactive o-quinodimethanes. In this embodiment, half-life values for the parent benzocyclobutene are calculated and summarized in the following Table 1, based on activation parameters reported in W. R. Roth et al Chem. Ber. 111, 3892–3903 (1978). The results suggest that reactive oligomers and polymers containing benzocyclobutenes which are not substituted at the cyclobutene ring would have long shelf-life and good reactivity at 200°–250° C.

TABLE 1

Benzocyclobutene $\xrightarrow{k}$ o-quinodimethane

| T (°C.) | k (sec$^{-1}$) | t$_\frac{1}{2}$ (hr) |
|---|---|---|
| 25 | 2.5 × 10$^{15}$ | 7.6 × 10$^{10}$ |
| 100 | 1.7 × 10$^{-9}$ | 1.1 × 10$^{5}$ |
| 150 | 9.6 × 10$^{-7}$ | 2 × 10$^{2}$ |
| 200 | 1.4 × 10$^{-4}$ | 1.4 |
| 250 | 7.8 × 10$^{-3}$ | 2.5 × 10$^{-2}$ |

ILLUSTRATIVE EMBODIMENT II 4,4'-ethylenedibenzocyclobutene (EDBC) was prepared according to a literature procedure.*[1] The FeCl$_3$-catalyzed coupling of 4-chloromethylbenzocyclobutene and its Grignard derivative gave a 65:35 mixture of EDBC and unreacted 4-chloromethylbenzocyclobutene. The contaminated EDBC was used to demonstrate the proposed curing chemistry.

[1]* G. D. Ewing and V. Boekelheide, Chem. Commun., 207 (1977).

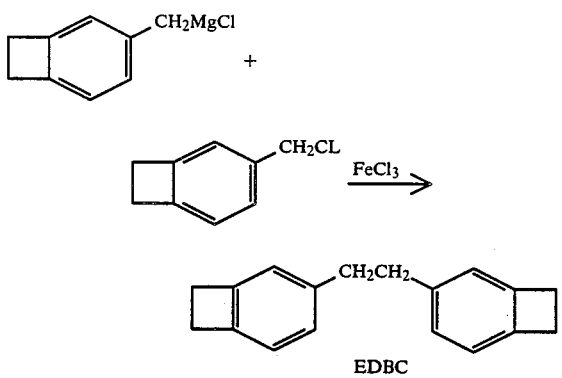

Blends of Nordel 1040 (a DuPont EPDM elastomer containing 0.34 meq/g of 1,4-hexadiene cure sites based on ozonolysis) and EDBC were prepared from hexane solutions. Curing was effected by compression molding at 200° C. for 24 h or 250° C. for 1 h. The heating times were significantly longer than the seven half-lives needed for 99% conversion of benzocyclobutenes to reactive o-xylylenes. The half-life values of benzocyclobutene have been reported to be 1.4 h at 200° C. and 1.5 min. at 250° C. Blends containing 20 phr and 30 phr EDBC per 100 phr Nordel 1040 gave vulcanizates with strengths comparable to a peroxide-Nordel 1040 compound (Table 2), whereas a blend with 10 phr EDBC resulted in poor strength. The relatively low efficiency of EDBC in effecting curing of EPDM may be attributed to competing homopolymerization of EDBC as indicated by electron microscopic analysis which shows the presence of aromatic rich dispersed spheres upon staining with $RuO_4$.

It should be noted that the proposed crosslinks in Nordel 1040-EDBC vulcanizates contain three different kinds of benzylic carbon-carbon bonds as shown below:

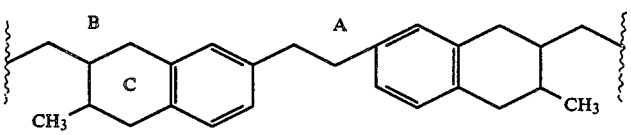

Benzylic carbon-carbon bonds are of 4 kcal/mole stronger than allylic carbon-carbon bonds (Table 3). Bond types B and C are formed as the result of the Diels-Alder curing chemistry; however, these do not represent weak links since both B and C would have to be cleaved in order to break the crosslink. Bond A is a potentially weak link, but it is part of the curing agent EDBC and not inherent to the curing chemistry. Replacement of the ethylene bridge in EDBC with phenyl or xylyl linkage would eliminate the potential weak links introduced by EDBC.

TABLE 2

| Tensile Properties (a) of EDBC-Nordel 1040 Vulcanizates | | | |
|---|---|---|---|
| Blend Composition | 200% Modulus (PSI) | Tensile Strength (PSI) | % Elongation at break |
| 100 phr Nordel 1040 20 phr EDBC | 135 ± 9.9 | 1043 ± 268 | 835 ± 105 |
| 100 phr Nordel 1040 30 phr EDBC | 153 ± 6.4 | 740 ± 314 | 562 ± 115 |

TABLE 2-continued

| Tensile Properties (a) of EDBC-Nordel 1040 Vulcanizates | | | |
|---|---|---|---|
| Blend Composition | 200% Modulus (PSI) | Tensile Strength (PSI) | % Elongation at break |
| 100 phr Nordel 1040 (b) 125 phr Carbon 50 phr Oil 5 phr ZnO 8 phr Di Cup 40° C. | 250 | 925 | 560 |

(a) Averages of three mini specimens measured at a crosshead speed of 1 in/min.
(b) Peroxide-cured compound. Data from "Peroxide Curing of Nordel", DuPont publication ND-310.2.

TABLE 3

| Carbon-Carbon Bond Dissociation Energy | |
|---|---|
| C—C Bond | Dissociation Energy (kcal/mole) (a) |
| Me—$CH_3$ | 88 |
| Me—$C_2H_5$ | 85 |
| Me—iPr | 84 |
| Me—tBu | 82 |
| Me—Ph | 100 |
| Me—Bz | 72 |
| Me—allyl | 68 |

(a) From CRC Handbook of Chemistry and Physics, 61st Edition; H. J. Harwood, JTEVA, 11, 289 (1983).

What is claimed is:

1. A polymeric composition which may be readily crosslinked at temperatures above about 200° C., said composition comprising an elastomeric polymer having olefinic unsaturation and an effective crosslinking amount of a benzocyclobutene derivative having the general formula

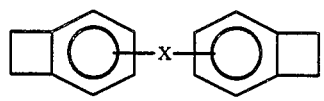

where "X" is selected from the group consisting of

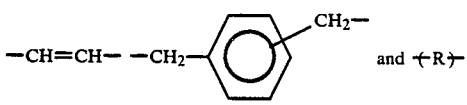

where "R" is an alkylene group of 1 to 10 carbon atoms.

2. The composition of claim 1 wherein said elastomeric polymer is selected from the group consisting of: ethylene/$C_3$ to $C_8$ alpha-monoolefin/diene monomer terpolymer, butyl rubber, polyisobutylene, polybutadiene, polyisoprene, styrene-butadiene rubber, nitrile rubber, neoprene rubber and styrene-butadiene block copolymers.

3. The composition of claim 2 wherein said elastomeric polymer is an ethylene/propylene/diene monomer terpolymer (EPDM).

4. The composition of claim 1 wherein said benzocyclobutene derivative is selected from the group consisting of:
4,4'-ethylenedibenzocyclobutene
4,4'-(p-xylylene)dibenzocyclobutene
4,4'-(o-xylylene)dibenzocyclobutene
4,4'-(m-xylylene)dibenzocyclobutene
3,3'-(p-xylylene)dibenzocyclobutene
3,3'-(o-xylylene)dibenzocyclobutene
3,3'-(m-xylylene)dibenzocyclobutene
4,3'-(p-xylylene)dibenzocyclobutene
4,3'-(o-xylylene)dibenzocyclobutene
4,3'-(m-xylylene)dibenzocyclobutene
4,4'-methylenedibenzocyclobutene
3,3'-methylenedibenzocyclobutene, and
4,3'-methylenedibenzocyclobutene.

5. The composition of claim 4 wherein said benzocyclobutene derivative is 4,4'-ethylenedibenzocyclobutene.

6. The composition of claim 3 wherein said benzocyclobutene derivative is 4,4'-ethylenedibenzocyclobutene.

7. The composition of claim 1 wherein the amount of benzocyclobutene derivative in said composition is between about 1 and about 30 parts by weight per 100 parts by weight of said elastomeric polymer.

8. The composition of claim 7 wherein the amount of benzocyclobutene derivative in said composition is between about 5 and about 20 parts by weight per 100 parts by weight of said elastomeric polymer.

9. A process for preparing a crosslinkable polymeric composition which comprises combining an elastomeric polymer having olefinic unsaturation with a benzocyclobutene derivative of the general formula

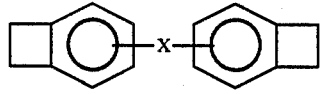

wherein "X" is selected from the group consisting of

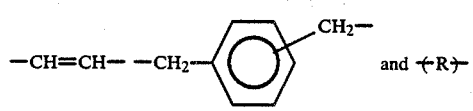

wherein "R" is an alkylene group of 1 to 10 carbon atoms, and in an amount effective for crosslinking the elastomeric polymer.

10. The process of claim 9 wherein the elastomeric polymer is an ethylene/propylene/diene monomer terpolymer (EPDM).

11. The process of claim 10 wherein the benzocyclobutene derivative is a 4,4'-ethylenedibenzocyclobutene.

12. The proces of claim 11 wherein the benzocyclobutene derivative is present in amount between about 1 and about 30 parts by weight per hundred parts by weight of said elastomeric polymer.

13. A process for preparing a polymeric composition which comprises combining an elastomeric polymer having olefinic unsaturation with a benzocyclobutene derivative of the general formula

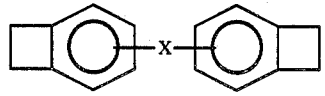

wherein "X" is selected from the group consisting of

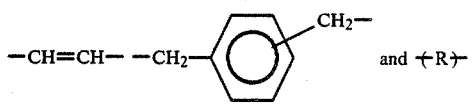

wherein "R" is an alkylene group of 1 to 10 carbon atoms, in an amount effective for crosslinking the elastomeric polymer, and heating the mixture at a temperature above about 200° C. for a time sufficient to crosslink the elastomeric polymer.

14. The process of claim 13 wherein the mixture is heated at a temperature between about 200° and about 300° C. for at least about 5 minutes.

15. The process of claim 13 wherein the elastomeric polymer is an ethylene/propylene/diene monomer terpolymer (EPDM).

16. The process of claim 15 wherein the benzocyclobutene derivative is a 4,4'-ethylenedibenzocyclobutene.

17. The process of claim 16 wherein the benzocyclobutene derivative is present in amount between about 1 and about 30 parts by weight per hundred parts by weight of said elastomeric polymer.

18. A polymeric composition prepared by the process of claim 13.

19. A polymeric composition prepared by the process of claim 14.

* * * * *